(12) United States Patent
Zhou et al.

(10) Patent No.: US 11,278,497 B2
(45) Date of Patent: Mar. 22, 2022

(54) CO-SPRAY DRYING OF MEROPENEM AND COLISTIN AND THE USES THEREOF

(71) Applicant: Purdue Research Foundation, West Lafayette, IN (US)

(72) Inventors: Qi Zhou, West Lafayette, IN (US); Sharad Mangal, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/395,303

(22) Filed: Apr. 26, 2019

(65) Prior Publication Data

US 2019/0328669 A1    Oct. 31, 2019

Related U.S. Application Data

(60) Provisional application No. 62/662,883, filed on Apr. 26, 2018.

(51) Int. Cl.
| | |
|---|---|
| *A61K 9/16* | (2006.01) |
| *A61K 9/00* | (2006.01) |
| *A61P 31/04* | (2006.01) |
| *A61K 38/12* | (2006.01) |
| *A61K 31/407* | (2006.01) |

(52) U.S. Cl.
CPC .......... *A61K 9/1688* (2013.01); *A61K 9/0075* (2013.01); *A61K 31/407* (2013.01); *A61K 38/12* (2013.01); *A61P 31/04* (2018.01)

(58) Field of Classification Search
CPC ......... A61K 9/14; A61K 38/12; A61K 31/407
See application file for complete search history.

(56) References Cited

FOREIGN PATENT DOCUMENTS

WO    WO-2016013986 A1  *  1/2016  .............. A61P 11/00

OTHER PUBLICATIONS

Fan et al. (Plos One, Jun. 17, 2016, pp. 1-12) (Year: 2016).*
Abdelkader, A., et al, "Ultrahigh antibacterial efficacy of meropenem-loaded chitosan nanoparticles in a septic animal model", Carbohydrate polymers, 174, 2017, pp. 1041-1050.
Cai, Y., et al, "Colistin resistance of Acinetobacter baumannii: clinical reports, mechanisms and antimicrobial strategies", Journal of Antimicrobial Chemotherapy, 67, 2012, pp. 1607-1615.
Ceilecka-Pointek, J., et al, "Solid-state stability study of meropenem—solutions based on spectrophotometric analysis", Chem. Cent. J. 7, 2013, pp. 98-98.
Feng, A., et al, "Mechanistic models facilitate efficient development of leucine containing microparticles for pulmonary drug delivery", Int. J. Pharm. 409, 2013, pp. 156-163.
Grasmeijer, F., et al, "New mechanisms to explain the effects of added lactose fines on the dispersion performance of adhesive mixtures for inhalation", PLoS One 9, 2014, e87825, pp. 11.
Jong, T., et al, "Investigation of the Changes in Aerosolization Behavior Between the Jet-Milled and Spray-Dried Colistin Powders Through Surface Energy Characterization", Journal of pharmaceutical sciences, 105, 2016, pp. 1156-1163.
Lenhard, J., et al, "High-intensity meropenem combinations with polymyxin B: new strategies to overcome carbapenem resistance in Acinetobacter baumannii", Journal of Antimicrobial Chemotherapy 72, 2017, pp. 153-165.
Lin, Y., et al, "Powder production and particle engineering for dry powder inhaler formulations", Curr. Pharm. Des. 21, 2015, pp. 3902-3916.
Mangal, S., et al, "Relationship between surface concentration of L-leucine and bulk powder properties in spray dried formulations", Eur. J. Pharm. Biopharm. 94, 2015, pp. 160-169.
Packzkowska, M., et al, "β-Cyclodextrin complexation as an effective drug delivery system for meropenem", European Journal of Pharmaceutics and Biopharmaceutics, 99, 2016, pp. 24-34.
Singh, A., et al, "Spray drying formulation of amorphous solid dispersions", Advanced Drug Delivery Reviews 100, 2016, pp. 27-50.
Sou, T., et al, "The effect of amino acid excipients on morphology and solid-state properties of multi-component spray-dried formulations for pulmonary delivery of biomacromolecules", European Journal of Pharmaceutics and Biopharmaceutics, 83, 2013, pp. 234-243.
Velkov, T., et al, "Inhaled anti-infective chemotherapy for respiratory tract infections: Successes, challenges and the road ahead", Advanced Drug Delivery Reviews, 85, 2015, pp. 65-82.
Zhou, Q., et al, "Characterization of the surface properties of a model pharmaceutical fine powder modified with a pharmaceutical lubricant to improve flow via a mechanical dry coating approach", J. Pharm. Sci. 100, 2011, pp. 3421-3430.
Zhou, Q., et al, "Synergistic Antibiotic Combination Powders of Colistin and Rifampicin Provide High Aerosolization Efficiency and Moisture Protection", The AAPS journal, 16, 2014, pp. 37-47.
Zhou, Q, et al, "Colistin Powders with High Aerosolisation Efficiency for Respiratory Infection: Preparation and In Vitro Evaluation", J. Pharm. Sci. 102, 2013, pp. 3736-3747.
Zhou, Q, et al, "How Much Surface Coating of Hydrophobic Azithromycin Is Sufficient to Prevent Moisture-Induced Decrease in Aerosolisation of Hygroscopic Amorphous Colistin Powder?", The AAPS 18, 2016, pp. 1213-1224.

* cited by examiner

*Primary Examiner* — Mark V Stevens
(74) *Attorney, Agent, or Firm* — Purdue Research Foundation; Liang Zeng Yan (57) ABSTRACT

The present disclosure generally relates to a process for manufacturing a dry powder composition, particularly to a co-sprayed colistin and meropenem dry powder inhaler for the treatment of various bacterial infections. Methods of use and composition matters are within the scope of this disclosure.

16 Claims, 6 Drawing Sheets

CO-SPRAY DRYING OF MEROPENEM AND COLISTIN AND THE USES THEREOF

CROSS REFERENCE TO RELATED APPLICATIONS

This present patent application relates to and claims the priority benefit of U.S. Provisional Application Ser. No. 62/662,883, filed Apr. 26, 2018, the content of which is hereby incorporated herein by reference in its entirety.

GOVERNMENT SUPPORT CLAUSE

This invention was made with government support under AI132681 awarded by the National Institutes of Health. The government has certain rights in the invention.

TECHNICAL FIELD

The present application relates generally to a process for manufacturing a dry powder inhaler formulation, and specifically to co-spray drying of meropenem and colistin to manufacture a dry powder composition for the treatment of a bacterial infection.

BACKGROUND

This section introduces aspects that may help facilitate a better understanding of the disclosure. Accordingly, these statements are to be read in this light and are not to be understood as admissions about what is or is not prior art.

Lower respiratory tract infections cause high mortality and morbidity (Mizgerd, J P, *PLoS Med.* 2006, 3, e76). Antibiotics administered via systemic routes are often not effective for lung infections, as for many antibiotics such as the polymyxins (polymyxin B and colistin) only a small fraction of the drug is available at the sites of infection i.e., the lungs (Velkov T, et al., *Adv. Drug Deliv. Rev.* 2015, 85, 65-82). Simply increasing parenteral dose often causes severe systemic adverse effects. For instance, high-dose parenteral colistin can lead to neurotoxicity and nephrotoxicity (Garonzik S M, et al., *Antimicrobial Agents and Chemotherapy* 2011, 55, 3284-3294).

Colistin is often used for treatment of respiratory infections caused by multidrug-resistant (MDR) Gram-negative bacteria. Recently, there is a marked increase in the incidences of colistin-resistant infections (Paterson and Harris, *Lancet* Infection Diseases 2016, 16, 132-133). Due to the dry development pipeline of novel antibiotics, combination therapy can be a practical and swift approach for treating the infections caused by colistin-resistant pathogens (Cai Y. et al., *J. Antimicrobial Chemotherapy* 2012, 67, 1607-1615). However, synergistic antibacterial effects of systemically administered combination antibiotics can be compromised due to the different pharmacokinetic profiles (Weers *J, Adv. Drug Deliv. Rev.* 2015, 85, 24-43), which may not allow both drugs to attain effective drug concentrations at the same time at the infection sites.

SUMMARY

In some illustrative embodiments, the present invention relates to a process for manufacturing a dry powder composition comprising the steps of a. dissolving colistin and meropenem, or a pharmaceutically acceptable salt thereof, respectively, in an aqueous medium to prepare a solution;

b. adding one or more pharmaceutically acceptable excipients to said solution; and c. spray-drying of said solution.

In some illustrative embodiments, the present invention relates to a process for manufacturing a dry powder composition disclosed herein, wherein said solution comprises colistin and meropenem in a ratio of about 1:10 to about 10:1(weight/weight).

In some illustrative embodiments, the present invention relates to a process for manufacturing a dry powder composition disclosed herein, wherein said solution comprises about 5 to 200 mg of colistin and meropenem in a ratio of about 1:10 to about 10:1 (weight/weight) per milliliter.

In some illustrative embodiments, the present invention relates to a process for manufacturing a dry powder composition disclosed herein, wherein said aqueous medium is water or an aqueous solution of an organic solvent selected from the group consisting of acetonitrile, methanol, ethanol, or isopropyl alcohol wherein said organic solvent is to improve the solubility of the solid drug materials which could not be fully dissolved in pure water.

In some other illustrative embodiments, the present invention relates to a dry powder composition manufactured according to the process disclosed herein.

In some other illustrative embodiments, the present invention relates to a dry powder composition manufactured according to the process disclosed herein, wherein colistin and meropenem are in a ratio of about 1:10 to about 10:1 (weight/weight).

In some other illustrative embodiments, the present invention relates to a pharmaceutical composition comprising the product manufactured according to the process disclosed herein, together with one or more pharmaceutically acceptable excipients.

In some other illustrative embodiments, the present invention relates to a pharmaceutical composition comprising the product manufactured according to the process disclosed herein, together with one or more pharmaceutically acceptable excipients, wherein colistin and meropenem are in a ratio of about 1:10 to about 10:1 (weight/weight).

In some other illustrative embodiments, the present invention relates to a pharmaceutical composition manufactured according to the process of:

a. dissolving colistin and meropenem, or a pharmaceutically acceptable salt thereof, respectively, in an aqueous medium to prepare a solution;

b. adding one or more pharmaceutically acceptable excipients to said solution; and c. spray-drying of said solution.

In some other illustrative embodiments, the present invention relates to a pharmaceutical composition comprising the product manufactured according to the process disclosed herein, together with one or more pharmaceutically acceptable excipients, wherein said solution of colistin and meropenem comprises about 5 to 200 mg of colistin and meropenem in a ratio of about 1:10 to about 10:1 (weight/weight) per milliliter.

In some other illustrative embodiments, the present invention relates to a pharmaceutical composition comprising the product manufactured according to the process disclosed herein, together with one or more pharmaceutically acceptable excipients, wherein said pharmaceutical composition is administered by inhalation.

In some other illustrative embodiments, the present invention relates to a method for treating a patient with a bacterial infection comprising the step of administering a therapeutically effective amount of the pharmaceutical composition disclosed herein, to a patient in need of relief from said infection.

In some other illustrative embodiments, the present invention relates to a method for treating a patient with a bacterial infection comprising the step of administering a therapeutically effective amount of the pharmaceutical composition disclosed herein, to a patient in need of relief from said infection, wherein said infection is an infection of the lungs.

In some other illustrative embodiments, the present invention relates to a method for treating a patient with a bacterial infection comprising the step of administering a therapeutically effective amount of the pharmaceutical composition disclosed herein, to a patient in need of relief from said infection, wherein said infection is caused by *Pseudomonas aeruginosa, Acinetobacter baumannii* and *Klebsiella pneumoniae*.

In some other illustrative embodiments, the present invention relates to a method for treating a patient with a bacterial infection comprising the step of administering a therapeutically effective amount of the pharmaceutical composition disclosed herein, to a patient in need of relief from said infection, wherein said pharmaceutical composition is administered by inhalation.

In some other illustrative embodiments, the present invention relates to a method for treating a patient with a bacterial infection comprising the step of administering a therapeutically effective amount of the dry powder inhaler composition disclosed herein, to a patient in need of relief from said infection, wherein said infection is an infection of the lungs.

In some other illustrative embodiments, the present invention relates to a method for treating a patient with a bacterial infection comprising the step of administering a therapeutically effective amount of the dry powder inhaler composition disclosed herein, to a patient in need of relief from said infection, wherein said infection is caused by *Pseudomonas aeruginosa, Acinetobacter baumannii* and *Klebsiella pneumoniae*.

In some other illustrative embodiments, the present invention relates to a method for treating a patient with a bacterial infection comprising the step of administering a therapeutically effective amount of the dry powder inhaler composition disclosed herein, to a patient in need of relief from said infection, wherein said dry powder inhaler composition is administered by inhalation.

In some other embodiments, colistin may be replaced with other polymyxins, such as polymyxins B. And in some other embodiments, meropenem may be replaced with an antibiotic from the group consisting of Doripenem, Ertapenem, Imipenem, Tebipenem, Biapenem, and Panipenem. Those polymyxins and carbapenem antibiotics and the pharmaceutically acceptable salts thereof, are within the scope of this disclosure.

These and other features, aspects and advantages of the present invention will become better understood with reference to the following figures, descriptions and claims.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 3A-Raw Meropenem; FIG. 3B—Colistin:Meropenem_1:3; FIG. 3C—Colistin:Meropenem_1:1; FIG. 3D-Colistin:Meropenem_3:1 and FIG. 3E—Raw Colistin (scale bar represents 10 μm).

FIG. 5A shows In-vitro aerosol performance of fine particle fraction (% FPF)

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In some illustrative embodiments, the present invention relates to a process for manufacturing a dry powder composition comprising the steps of
 a. dissolving colistin and meropenem, or a pharmaceutically acceptable salt thereof, respectively, in an aqueous medium to prepare a solution;
 b. adding one or more pharmaceutically acceptable excipients to said solution; and
 c. spray-drying of said solution.

In some illustrative embodiments, the present invention relates to a process for manufacturing a dry powder composition disclosed herein, wherein said solution comprises colistin and meropenem in a ratio of about 1:10 to about 10:1 (weight/weight).

In some illustrative embodiments, the present invention relates to a process for manufacturing a dry powder composition disclosed herein, wherein said solution comprises about 5 to 200 mg of colistin and meropenem in a ratio of about 1:10 to about 10:1 (weight/weight) per milliliter.

In some illustrative embodiments, the present invention relates to a process for manufacturing a dry powder composition disclosed herein, wherein said aqueous medium is water or an aqueous solution of an organic solvent selected from the group consisting of acetonitrile, methanol, ethanol, or isopropyl alcohol wherein said organic solvent is to improve the solubility of the solid drug materials which could not be fully dissolved in pure water.

In some other illustrative embodiments, the present invention relates to a dry powder composition manufactured according to the process disclosed herein.

In some other illustrative embodiments, the present invention relates to a dry powder composition manufactured according to the process disclosed herein, wherein colistin and meropenem are in a ratio of about 1:10 to about 10:1 (weight/weight).

In some other illustrative embodiments, the present invention relates to a pharmaceutical composition comprising the product manufactured according to the process disclosed herein, together with one or more pharmaceutically acceptable excipients.

In some other illustrative embodiments, the present invention relates to a pharmaceutical composition comprising the product manufactured according to the process disclosed herein, together with one or more pharmaceutically acceptable excipients, wherein colistin and meropenem are in a ratio of about 1:10 to about 10:1 (weight/weight).

In some other illustrative embodiments, the present invention relates to a pharmaceutical composition manufactured according to the process of:
  a. dissolving colistin and meropenem, or a pharmaceutically acceptable salt thereof, respectively, in an aqueous medium to prepare a solution;
  b. adding one or more pharmaceutically acceptable excipients to said solution; and
  c. spray-drying of said solution.

In some other illustrative embodiments, the present invention relates to a pharmaceutical composition comprising the product manufactured according to the process disclosed herein, together with one or more pharmaceutically acceptable excipients, wherein said solution of colistin and meropenem comprises about 5 to 200 mg of colistin and meropenem in a ratio of about 1:10 to about 10:1 (weight/weight) per milliliter.

In some other illustrative embodiments, the present invention relates to a pharmaceutical composition comprising the product manufactured according to the process disclosed herein, together with one or more pharmaceutically acceptable excipients, wherein said pharmaceutical composition is administered by inhalation.

In some other illustrative embodiments, the present invention relates to a method for treating a patient with a bacterial infection comprising the step of administering a therapeutically effective amount of the pharmaceutical composition disclosed herein, to a patient in need of relief from said infection.

In some other illustrative embodiments, the present invention relates to a method for treating a patient with a bacterial infection comprising the step of administering a therapeutically effective amount of the pharmaceutical composition disclosed herein, to a patient in need of relief from said infection, wherein said infection is an infection of the lungs.

In some other illustrative embodiments, the present invention relates to a method for treating a patient with a bacterial infection comprising the step of administering a therapeutically effective amount of the pharmaceutical composition disclosed herein, to a patient in need of relief from said infection, wherein said infection is caused by *Pseudomonas aeruginosa*, *Acinetobacter baumannii* and *Klebsiella pneumoniae*.

In some other illustrative embodiments, the present invention relates to a method for treating a patient with a bacterial infection comprising the step of administering a therapeutically effective amount of the pharmaceutical composition disclosed herein, to a patient in need of relief from said infection, wherein said pharmaceutical composition is administered by inhalation.

In some other illustrative embodiments, the present invention relates to a method for treating a patient with a bacterial infection comprising the step of administering a therapeutically effective amount of the dry powder inhaler composition disclosed herein, to a patient in need of relief from said infection, wherein said infection is an infection of the lungs.

In some other illustrative embodiments, the present invention relates to a method for treating a patient with a bacterial infection comprising the step of administering a therapeutically effective amount of the dry powder inhaler composition disclosed herein, to a patient in need of relief from said infection, wherein said infection is caused by *Pseudomonas aeruginosa*, *Acinetobacter baumannii* and *Klebsiella pneumoniae*.

In some other illustrative embodiments, the present invention relates to a method for treating a patient with a bacterial infection comprising the step of administering a therapeutically effective amount of the dry powder inhaler composition disclosed herein, to a patient in need of relief from said infection, wherein said dry powder inhaler composition is administered by inhalation.

In some other embodiments, colistin may be replaced with other polymyxins, such as polymyxins B. And in some other embodiments, meropenem may be replaced with an antibiotic from the group consisting of Doripenem, Ertapenem, Imipenem, Tebipenem, Biapenem, and Panipenem. Those polymyxins and carbapenem antibiotics and the pharmaceutically acceptable salts thereof, are within the scope of this disclosure.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

Antimicrobial therapy via the inhalation route has attracted increasing momentum for the treatment of lower respiratory infections (Zhou Q. et al., *Adv. Drug Deliv. Rev.* 2015, 85, 83-99). Inhalation therapy substantially improves drug concentration on the airway surfaces with much reduced systemic exposure, hence maximizes the treatment efficacy and reduces the systemic toxicities. Additionally, inhalation therapy may be able to deliver combinational antibiotics to the same targeted infection sites simultaneously allowing greater opportunity to achieve intended synergistic effects. In addition, dry powder inhalers (DPIs) may enable delivery of high-doses of antibiotics directly to the respiratory tract.

Typically, the inhaled drug particles produced by traditional jet-milling approach are highly cohesive and have poor flowability and poor aerosolization performance. Addition of excipients such as fine lactose particles may improve the aerosolization of cohesive powders to some extent (Grasmeijer F. et al., *PLoS One* 2014, 9, e87825). However, for high-dose drugs like antibiotics, addition of excipients may increase the inhalation powder mass that needs an excessive number of inhalations to complete the dose and a bulky inhaler to accommodate the large dose.

Our earlier studies have indicated that the spray dried colistin particles without any excipient had high aerosol performance with fine particle fraction (FPF)>80%. It was proposed that such high aerosol performance of the spray dried colistin powders is attributed to its surfactant-like properties, which allows self-assembly of non-polar tail at the air interface during spray drying resulting in the formation of low surface energy particles (Jong T, et al., *J. Pharm. Sci.* 2016, 105, 1156-1163). Previous studies have shown that surface-active components could also potentially self-assemble on the surface, when co-sprayed with a secondary component altering its surface physico-chemical and aerosolization properties (Zhou Q. et al., *AAPS J.* 2016, 18, 1213-1224). The aim of this study was to investigate the effect of colistin on the aerosol performance of the co-spray dried formulations in synergistic combination with meropenem (Lenhard J R, et al., *J. Antimicrobial Chemotherapy* 2016, 72, 153-165).

To this end, colistin was co-spray dried with meropenem to develop combinational DPI formulations. The resultant DPI formulations were characterized regarding particle size, morphology, surface chemical composition and specific surface area. The in-vitro aerosol performance and antibacterial activity were characterized.

Polymyxins are peptide antibiotics, such as polymyxins B and E (also known as colistin), widely used in the treatment of Gram-negative bacterial infections. They work mostly by breaking up the bacterial cell membrane. They are part of a broader class of molecules called nonribosomal peptides. Meropenem is a broad-spectrum, carbapenem family antibiotics antibiotic used to treat a variety of bacterial infections. Other antibiotics in this family include Doripenem, Ertapenem, Imipenem, Tebipenem, Biapenem, and Panipenem. Those polymyxins and carbapenem antibiotics and the pharmaceutically acceptable salts thereof, are within the scope of this disclosure.

Time Kill Assay

Figure 1A:
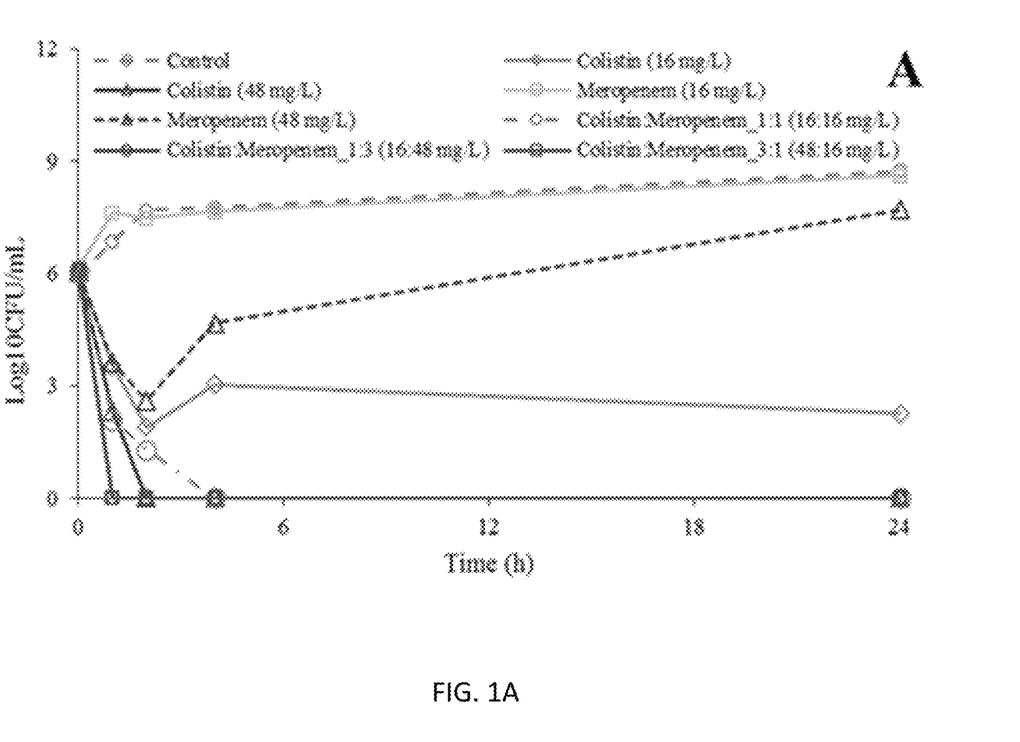
FIG. 1A demonstrates time-killing kinetics of colistin, meropenem and their combinations against *A. baumannii* N16870 (A)
Figure 1B:
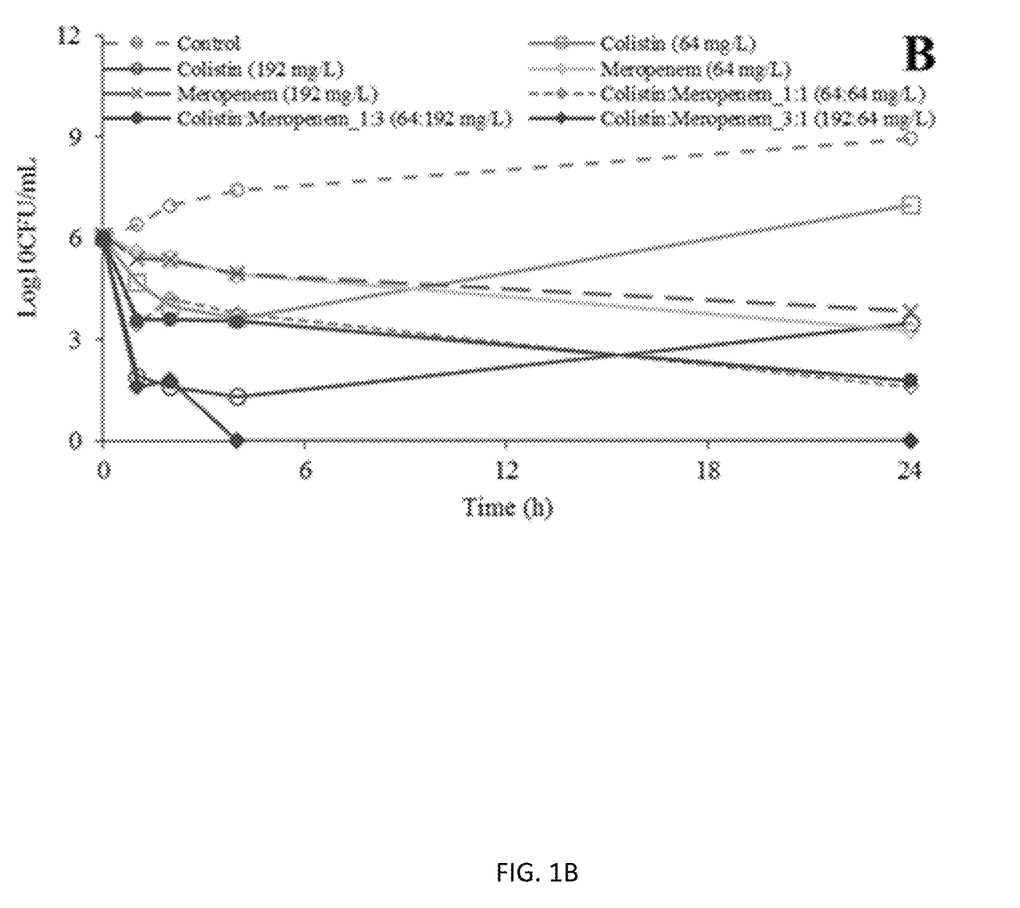
FIG. 1B demonstrates time-killing kinetics of colistin, meropenem and their combinations against *P. aeruginosa* 19147 (B).

FIG. 1 shows the time-kill profiles against clinical isolates of *A. baumannii* N16870 and *P. aeruginosa* 19147. For *A. baumannii* N16870, meropenem showed no antibacterial effect at 16 mg/L in 24 h, and marginal antibacterial activity at 48 mg/L in 2 h, albeit regrowth was observed in 4 h (FIG. 1A). Colistin showed bacterial killing at both 16 and 48 mg/L, but at 16 mg/L regrowth was evident in 4 h. The combination of Colistin:Meropenem_1:1 (16:16 mg/L) demonstrated superior antibacterial activity than monotherapy with each drug. Colistin:Meropenem_1:3 (16 and 48 mg/L) and Colistin:Meropenem_3:1 (48 and 16 mg/L) showed more rapid killing kinetics than meropenem or colistin alone. It is noteworthy that all three combinations demonstrated eradication of the bacteria without any regrowth.

The antibacterial activity of the colistin and meropenem appeared to be weaker against *P. aeruginosa* 19147 (FIG. 1B), even at a much higher concentrations (e.g. 192 mg/L), complete killing could not be achieved by either colistin or meropenem monotherapy at 24 h. The combination of Colistin:Meropenem_1:1 (64:64 mg/L) and Colistin:Meropenem_1:3 (64:192 mg/L) also did not achieve a complete bacterial killing after 24 h. A complete bacterial killing was observed only with the Colistin:Meropenem_3:1 (192:64 mg/L). These data show the difficulty in eradication of colistin-resistant strains of *A. baumannii* and *P. aeruginosa*. This is in agreement with previous studies indicating the antibacterial synergy between meropenem and colistin against multi-drug resistance pathogens.

Scanning Electron Microscopy (SEM)

Figure 2A:
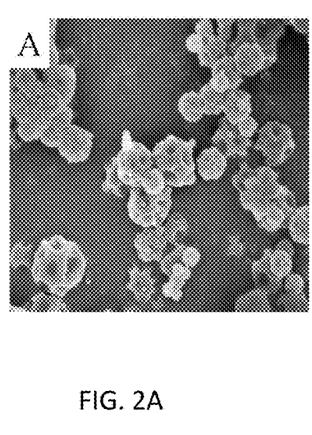
FIGS. 2A-2E depict representative scanning electron microscopy images of: Meropenem-SD (FIG. 2A); Colistin:Meropenem_1:3 (FIG. 2B); Colistin:Meropenem_1:1 (FIG. 2C); Colistin:Meropenem_3:1 (FIG. 2D); and Colistin-SD (FIG. 2E). Red arrows point out smooth particles (hollow or flake).
Figure 2B:
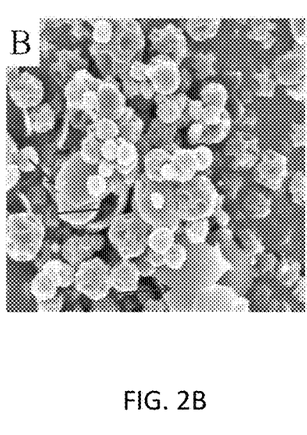
Figure 2C:
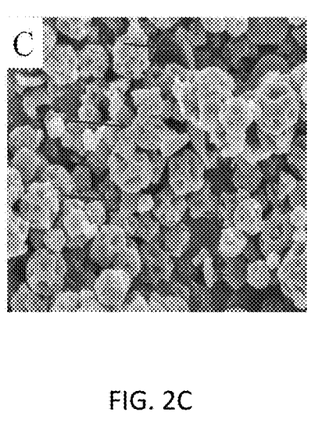
Figure 2D:
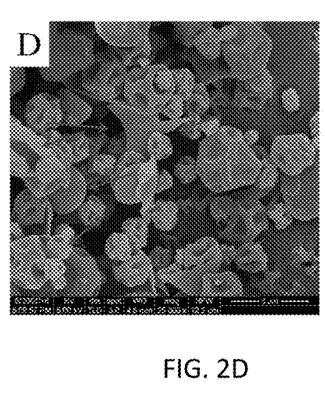
Figure 2E:
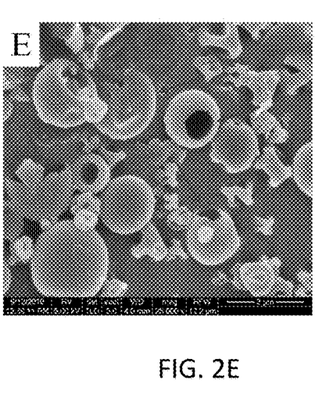
Figure 3A:
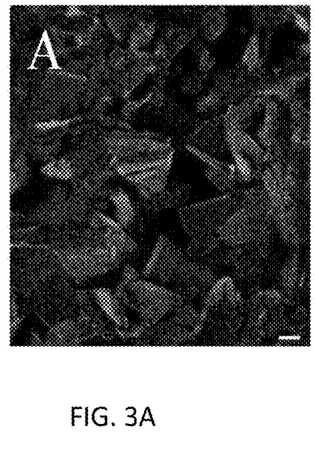
FIGS. 3A-3E depict surface composition distributions of colistin (red) and meropenem (green) on the surfaces of composite particles obtained by ToF-SIMS.
Figure 3B:
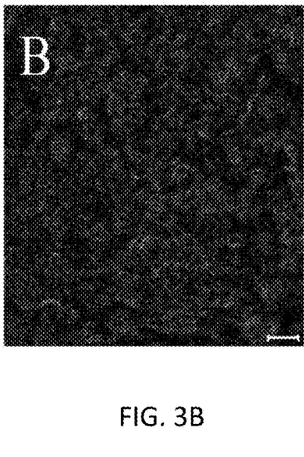
Figure 3C:
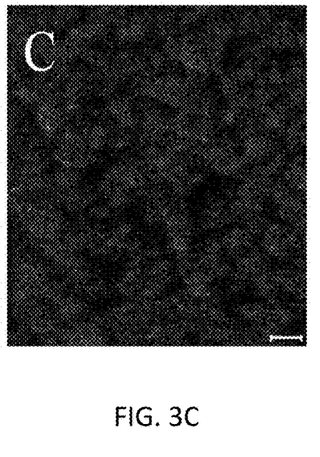
Figure 3D:
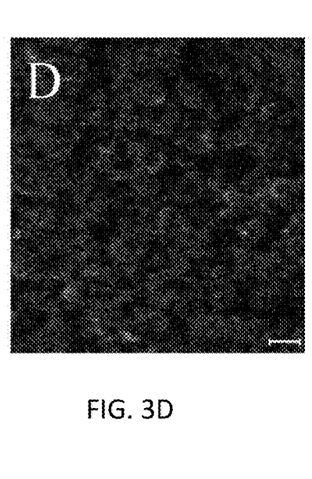
Figure 3E:
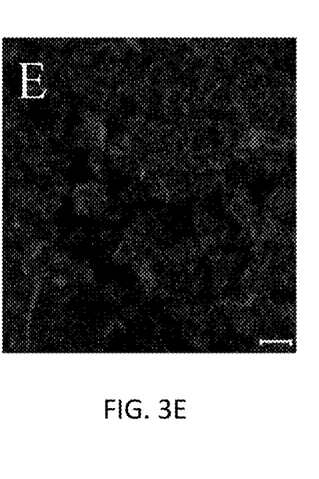

SEM images showed that the spray-dried meropenem particles are near-spherical with rough surfaces (FIG. 2A); while the spray-dried colistin particles showed a mixed population of rough and smooth (hollow or flake) particles as indicated by red arrows (FIG. 2E). Morphology of the co-spray dried formulations changed substantially with varying colistin concentrations. Colistin:Meropenem_1:3 showed more proportion of rough particles (FIG. 2B) than Colistin:Meropenem_1:1 (FIG. 2D). The population of hollow- or flake-shaped particles appeared to increase with increasing feed colistin concentrations (as shown by red arrows). Apparently, the flake-shaped particles are the fragments of shattered hollow particles.

Particle Size Distribution

Particle sizes of the spray-dried formulations are presented in Table 1. The results indicated that the $D_{50}$ of spray-dried formulations was <2 μm and $D_{90}$ was <3 μm. Therefore, the majority of particles were within the physical size range of 0.5-3 μm with no significant differences among formulations.

TABLE 1

Particle sizes of the spray-dried powder formulations.

| Formulation | Particle Size (μm) | | |
|---|---|---|---|
| | $D_{10}$ | $D_{50}$ | $D_{90}$ |
| Meropenem-SD | 0.8 ± 0.1 | 1.1 ± 0.1 | 1.9 ± 0.3 |
| Colistin-Meropenem_1:3 | 1.0 ± 0.2 | 1.4 ± 0.1 | 2.1 ± 0.3 |
| Colistin-Meropenem_1:1 | 1.0 ± 0.1 | 1.2 ± 0.1 | 1.5 ± 0.4 |
| Colistin-Meropenem_3:1 | 0.8 ± 0.1 | 1.2 ± 0.1 | 1.7 ± 0.1 |
| Colistin-SD | 1.0 ± 0.2 | 1.5 ± 0.1 | 2.7 ± 0.3 |

TABLE 2

Specific surface area and pore volume of spray-dried formulations. The data are presented as mean ± SD (n = 3).

| Formulation | Specific surface area ($m^2/g$) | Pore volume ($cm^3/g$) |
|---|---|---|
| Meropenem-SD | 3.1 ± 0.2 | 0.005 ± 0.001 |
| Colistin:Meropenem_1:3 | 4.8 ± 0.1 | 0.009 ± 0.001 |
| Colistin:Meropenem_1:1 | 5.4 ± 0.1 | 0.010 ± 0.001 |
| Colistin:Meropenem_3:1 | 6.6 ± 0.2 | 0.012 ± 0.001 |
| Colistin-SD | 7.2 ± 0.1 | 0.013 ± 0.001 |

Specific Surface Area and Pore Volume

Table 2 shows the specific surface area and pore volume of the selected spray-dried formulations. The surface area and pore volume increased substantially with increasing colistin feed proportion. The increase in surface area is likely attributed to the formation of porous particles, which have larger surface area than the non-porous particles.

Time-of-Flight Secondary Ion Mass Spectrometry (ToF-SIMS)

To-SIMS images of the spray-dried formulations clearly showed that the surface composition changed substantially with varying colistin concentration (FIGS. 3A-3E). Colistin: Meropenem_1:3 particles showed an abundance of both colistin and meropenem on the surfaces (FIG. 3B). The abundance of colistin on the particle surface was increased with an increase in colistin ratio in the combination formulations. It was noted that colistin dominated the particles surfaces in the Colistin:Meropenem_3:1 formulation (FIG. 3D).

X-Ray Photoelectron Spectroscopy (XPS)

Previous studies have suggested that surfactant-like molecules attains higher surface concentration due to their self-assembly at the air-water interface early in drying phase (Vehring, R. *Pharm. Res.* 2008, 25, 999-1022; Vehring R, et al., *J. Aerosol Sci.* 2007, 38, 728-746). Since, colistin exhibit surfactant-like properties, we compared colistin and meropenem composition of selected formulations with those determined at the surface by XPS (Table 4). In agreement with the ToF-SIMS data, the XPS results also demonstrated that the surface concentration of colistin increased with an increase in colistin feed concentration (Table 3). The surface concentration of colistin was 46.8% for the Colistin:Meropenem_1:3, which increased markedly to 67.6% and 87.7% for Colistin:Meropenem_1:1 and Colistin:Meropenem_3:1, respectively. Consistent with our hypothesis, colistin achieved higher surface concentration compared with the theoretical value (where a homogeneous distribution of colistin and meropenem is assumed on the particle surfaces), suggesting enrichment of colistin on the surface of the spray dried particles.

We also investigated the relationship between colistin surface composition and specific surface area/pore volume as obtained by BET (FIGS. 3A-3E). The graph clearly shows that the surface area and pore volume increased with increasing surface colistin composition. The formation of porous particles may be attributed to the enrichment of colistin at the surface of the composite particles.

We hypothesize that the self-assembly of colistin at the air-water interface creates an environment to hinder the escape of water vapour from the bulk of the droplet leading to an increased vapour pressure. An increase in vapour pressure results in expansion of the colistin-rich interface and eventual burst of particles leading to formation of porous/ruptured particles. The observation that porosity and surface area increased linearly with increasing surface concentration suggests that surface concentration governs the degree of resistance to the escape of water vapour, where a higher concentration results in higher resistance intensifying particle rupture leading to the formation of more porous particles with higher surface area.

TABLE 3

Molar composition of colistin and meropenem on the surfaces of composite formulations based on theoretical calculation and XPS measurement.

| Formulation | % Theoretical Composition | | % Measured Surface Composition | |
|---|---|---|---|---|
| | Colistin | Meropenem | Colistin | Meropenem |
| Colistin:Meropenem_1:3 | 26.0 | 74.0 | 46.8 | 53.2 |
| Colistin:Meropenem_1:1 | 51.4 | 48.6 | 67.6 | 32.4 |
| Colistin:Meropenem_3:1 | 76.0 | 24.0 | 87.7 | 12.3 |

Fourier Transform Infrared Spectroscopy (FTIR)

Potential molecular interactions between colistin and meropenem in the formulations were investigated by FTIR (Table 4). Distinguishable characteristic FTIR absorbance peaks identified for the spray-dried colistin were at 1645.0 cm (characteristic of the amide I C=O stretching), at 1525.4 cm (characteristic of the amide II N—H bending) and at 1068.4 cm (characteristic of stretching vibrations related to C—N). For the spray-dried meropenem, the stretching vibration peak of O—H in carboxylic acid group was observed at 2965.9 cm$^{-1}$. The distinguishable peaks from the stretching vibrations of the C=O in the carboxyl group and β-lactam ring were observed at 1658.5 and 1756.8 cm$^{-1}$, respectively. The stretching vibrations of the C—N bond in the pyrrolidine ring, β-lactam ring and dimethylcarbamoyl group were observed at 1145.5, 1253.5 and 1373.1 cm$^{-1}$, respectively. In addition, the wagging and twisting vibrations of the C—H bonds in the hydroxyethyl substituent and the β-lactam ring were observed at around 1070 cm$^{-1}$.

ethyl substituent and the β-lactam ring disappeared. In contrast, there were no significant change in the stretching vibrations peaks of C=O and C—N in the β-lactam ring. The peaks of colistin that correspond to the stretching vibrations of amide I C=O stretching and amide II N—H bending were shifted to the higher wavenumbers of 1650.8 and 1531.2 cm$^{-1}$, respectively. In addition, the C—N stretching vibrations were shifted to a higher wave number of 1074.1 cm$^{-1}$.

Powder X-Ray Diffraction (PXRD)

Raw meropenem was crystalline as evident by the sharp diffraction peaks of Powder X-ray diffraction (PXRD). PXRD patterns indicated that both the raw and spray-dried colistin were amorphous. Meropenem was transformed from crystalline form to amorphous form after spray drying, which is attributed to rapid drying that leads to random orientation of meropenem molecules in the dried phase (Singh and Van den Mooter, *Adv. Drug Deliv. Rev.* 2016, 100, 27-50). Furthermore, the spray-dried combination formulations also showed no sharp peaks indicating that they are all amorphous and the phase separation on the particle surface as indicated by XPS was not a consequence of crystallization as noted in an earlier study (Feng A L, et al., *Int. J. Pharm.* 2011, 409, 156-163).

In-Vitro Aerosol Performance

Figure 5A:
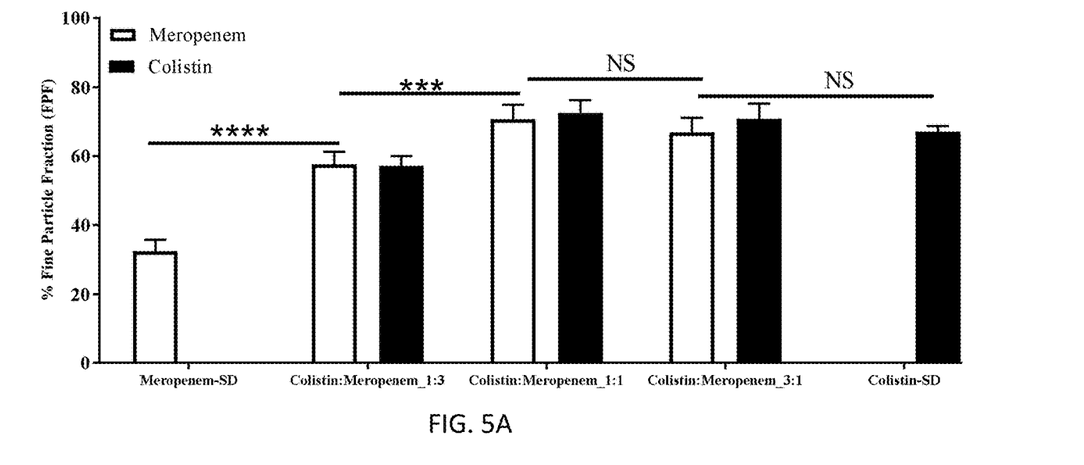
Figure 5B:
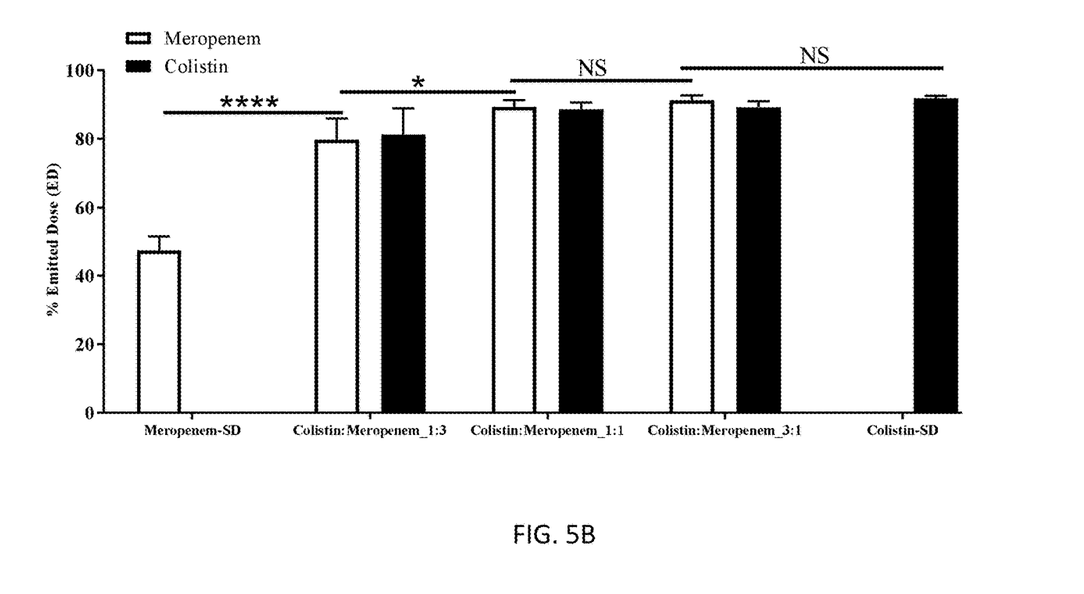
FIG. 5B shows emitted dose (% ED) of the spray-dried formulations. The data are presented as mean±SD (n=4).

In-vitro aerosol performance indicated by FPF and ED of the spray-dried powders are shown in FIGS. 5A-5B. The results show that the spray-dried meropenem had a relative low FPF of 32.4±3.3% indicating poor aerosolization performance. All the combination formulations showed a substantially higher FPF for both colistin and meropenem than the spray-dried meropenem (p<0.0001). Colistin:Meropenem_1:1 and Colistin:Meropenem_3:1 had the similar high FPF to the spray dried pure colistin formulation, which were more than two-fold of that for the spray-dried meropenem. Further increase in the colistin feed concentration from Colistin:Meropenem_1:1 to Colistin:Meropenem_3:1 had no significant effects in FPF. Furthermore, the ED of Mero-

TABLE 4

FTIR band assignment of various spray-dried formulations

| | | Wavenumber (cm$^{-1}$) | | |
|---|---|---|---|---|
| | Band assignment | Colistin | Colistin:Meropenem_1:1 | Meropenem |
| Colistin | C—N stretching | 1068.4 | 1074.1 | NA |
| | Amide II N—H bending | 1525.4 | 1531.2 | |
| | Amide I C=O stretching | 1645.0 | 1650.8 | |
| Mero-penem | Carboxyl C=O stretching | NA | 1650.8 | 1658.5 |
| | β-lactam C=O stretching | | 1758.7 | 1756.8 |
| | Dimethylcarbamoyl C—N stretching | | 1380.8 | 1373.1 |
| | β-lactam C—N stretching | | 1255.4 | 1253.5 |
| | Pyrrolidine C—N stretching | | 1139.7 | 1145.5 |
| | Hydroxyethyl and β-lactam C—H wagging and twisting | | 1074.1 | 1095.4 |
| | | | | 1072.2 |
| | | | | 1051.0 |

In the co-spray dried 1:1 mixture of meropenem and colistin, there were significant changes in the IR spectra compared to each spray dried pure component. The meropenem peaks that correspond to the stretching vibrations of O—H and C=O in the carboxyl group were shifted to lower wavenumbers of 2958.2 and 1650.8 cm$^{-1}$, respectively. In addition, the C—N stretching vibrations in the pyrrolidine ring and dimethylcarbamoyl group were shifted to 1139.7 and 1380.8 cm$^{-1}$, respectively. The multiple peaks of wagging and twisting vibrations of the C—H in the hydroxypenem-SD was as low as 47.3±4.3%, which was substantially lower than the spray dried colistin and the composite formulations (p<0.0001). Moreover, colistin and meropenem had identical FPF or aerosol performance in each composite formulation.

Our time-kill results against the clinical isolate *A. baumannii* N16870 and *P. aeruginosa* 19147 demonstrated that colistin and meropenem monotherapy showed weak antibacterial activity and considerable regrowth was observed (except for *A. baumannii* N16870 treated with colistin at 48 mg/L). The combinations exhibited excellent antibacterial activity against *A. baumannii* N16870. In the case of *P. aeruginosa* 19147, complete bacterial killing was achieved with Colistin:Meropenem_3:1 (192:64 mg/L). This indicates that high local concentrations of antibiotics are required to achieve effective bacterial killing for certain Gram-negative species. However, in most cases such high concentrations of antibiotics in airway surfaces deep in the lungs cannot be achieve by systemic administration (Garonzik et al., 2011). The inhalation route offers direct access of the drug to the lungs and hence may be more suitable for treating respiratory tract infections caused by MDR Gram-negative bacteria "superbugs" (Velkov et al., 2015; Zhou et al., 2015). In this study, for the first time we developed and characterized colistin and meropenem co-sprayed DPI formulations for the treatment of lower respiratory tract infections.

The spray dried colistin alone particles have two types of shapes: (i) smooth (some buckling) and hollow particles (ii) corrugated particles, which are in agreement with previous studies (Jong et al., *J. Pharm. Sci.* 2016, 105, 1156-1163). It seems lower inlet temperatures (e.g. 80° C.) resulted in more particles with corrugated morphology; while higher inlet temperature led to more hollow particles with smooth surfaces as shown in this study. This may be attributed to surfactant-like properties of colistin. When drying temperature is high, a shell of colistin is formed on the interface, and solutes cannot diffuse towards the core due to rapid drying (Vehring, 2008). In the drying process, wrinkled particles are formed because of initial high internal pressures due to solvent evaporation and then a decreased internal pressure leads to collapse of the shells. Some hollow particles are buckling because low colistin concentration leads to thin shell and high internal pressure causes rapture of the shell. This explains well that a higher drying temperature leads to more cenospheres or buckling particles attributed to more rapid evaporation of the solvent and higher internal pressure.

It is noted that colistin was more enriched on the particle surface than meropenem as shown by XPS data (Table 3). Meropenem has relatively lower water solubility (approximately 16.4 mg/mL), and usually less water soluble component can accumulate on the particle surfaces during drying as the compound with lower solubility will reach supersaturation and precipitate quicker on the surface than the compound with higher solubility (Vehring et al., 2007). However, surfactant-like molecules such as colistin can self-assemble at the air-water interface leading to shell formation (Mangal et al., *Eur. J. Pharm. Biopharm.* 2016, 104, 110-116). Spray-dried colistin particles exhibits a lower surface energy than the jet-milled colistin, attributed to the self-assembly of colistin at the air water interface with a specific orientation with low energy hydrophobic tail facing outwards (Jong et al., 2016). Despite its lower aqueous solubility, meropenem did not enrich at the surface indicating that interfacial activity may be the dominant factor governing the surface enrichment in composite spray-dried formulations, which warrants further investigation.

Figure 4A:
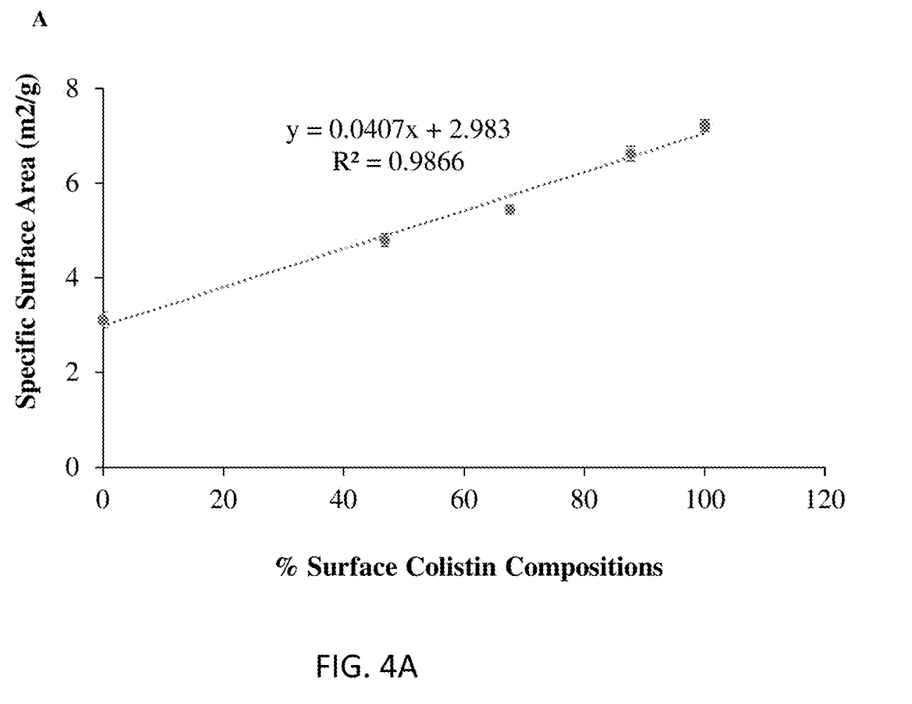
FIG. 4A shows the specific surface area of spray-dried formulations as a function of % surface colistin composition.
Figure 4B:
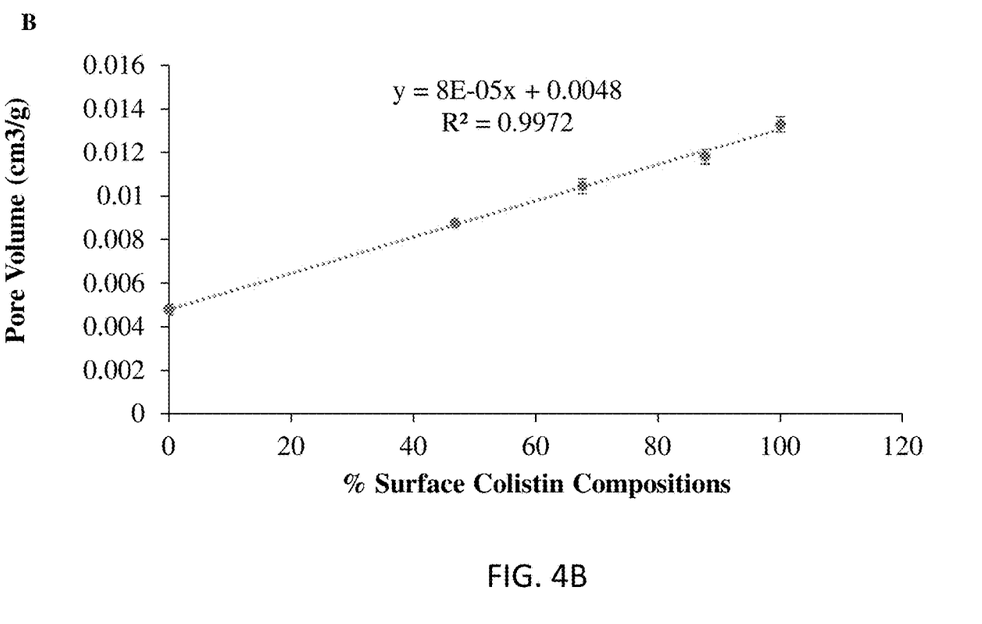
FIG. 4B shows the pore volume (B) of spray-dried formulations as a function of % surface colistin composition.

The shell forming ability of colistin may alter the morphology, porosity and surface area of co-sprayed formulations, and therefore affects the aerosolization (Chew and Chan, *J. Aerosol Med.* 2002, 15, 325-330). Our results clearly showed strong correlations between surface colistin concentration, surface area and porosity of the composite formulations (FIGS. 4A-4B), indicating that surface colistin concentration governs the bulk particle properties. As discussed earlier, such porous particles are produced as a consequence of colistin's shell formation during droplet drying. Spray-dried meropenem showed poor aerosolization performance, while, spray-dried colistin showed superior aerosolization performance, which was attributed to its low-cohesive propensity. Co-spraying with colistin improved the FPF of meropenem and Colistin-Meropenem_1:1 and Colistin-Meropenem_3:1 showed more than two-fold higher fine particle fraction compared with spray-dried meropenem. This suggests that colistin exerts an aerosolization-enhancing effect. Morphologically, co-sprayed formulations appeared similar to spray-dried meropenem; however, porosity increased with an increase in colistin concentration. Porous particles with low density have lower aerodynamic diameters than those with the same geometric diameters but higher density, which lead to better aerosolization performance of these colistin-containing composite formulations (Telko and Hickey, *Respir. Care* 2005, 50, 1209-1227).

It is interesting to note that some interactions between colistin and meropenem as demonstrated by the FT-IR data (Table 4). The changes in spectra were very significant for the formulation at the mass ratio of colistin to meropenem 1:1. In particular, the most notable change in spectra is that the O—H stretching band of the carboxyl group in meropenem shifted to the lower wavenumber. This kind of hydrogen bond is called red-shifting hydrogen bond which may be attributed to the lengthening and weakening of O—H bond due to the its attraction to hydrogen acceptor. At the same time, the amide I C=O band of colistin is shifted to the higher wavenumber. From these spectral changes, it can be suggested that there is a hydrogen bond between the carboxyl O—H group of meropenem as a hydrogen donor and C=O groups of colistin as a hydrogen acceptor. This hypothesis can be supported by the fact that the amide II N—H bending was shifted to the higher wavenumber with a decreased intensity, which can be observed when the N—H is not involved in an interaction with hydrogen acceptor, but other group bonded to N, such as carbonyl, is involved in hydrogen bond as an acceptor. In addition, there were also significant band shifts of meropenem not only in the C—H wagging and twisting vibrations in the hydroxyethyl substituent and the 3-lactam ring, but also in C—N stretching vibration in the pyrrolidine ring and dimethylcarbamoyl group, which indicate the change of overall structural conformation due to the forming of hydrogen bonding as reported previously (Paczkowska M, et al., *Eur. J. Pharm. Biopharm.* 2016, 99, 24-34). All those changes in FTIR spectrum could be a firm evidence for explanation of the intermolecular interactions via hydrogen bond between meropenem and colistin. Furthermore, FTIR result accompanied with the results of XPS and aerosolization performance suggest that the uniform distribution of colistin at the surface of co-spray dried particles likely led to the aerosolization-enhancing effect.

Conclusions—

In the present study, we developed and characterized co-spray dried colistin and meropenem DPI formulations which showed superior antibacterial activity. Incorporation of colistin improved the aerosolization performance of meropenem as evidenced by an almost two-fold increase in FPF, attributable to the enrichment of colistin on the particle surface and the increased porosity. FT-IR spectra demonstrated intermolecular interactions between colistin and meropenem. Such synergistic antimicrobial activities and increased aerosolization performance will not only improve the patient compliance by reducing the inhaled powder mass and minimizing local adverse effects, but also have potential to achieve superior therapeutic efficacy, which deserve further in-vivo studies using an established animal lung infection model.

Materials and Methods

Colistin sulphate and meropenem trihydrate were purchased from ßetaPharma® (Shanghai) Co., Ltd (Wujiang City, JiangSu Province, China). Acetonitrile (HPLC grade) was purchased from Merck (Fair Lawn, N.J.).

Time-Killing Assays

Clinical isolates of *A. baumannii* N16870 (colistin minimum inhibitory concentration [MIC] 0.5 mg/L; meropenem MIC 16 mg/L) and *Pseudomonas aeruginosa* 19147 (colistin MIC 0.5 mg/L; meropenem MIC 16 mg/L) were stored in tryptone soy broth with 20% glycerol at −80° C. and sub-cultured onto nutrient agar plates before each experiment. Time-kill studies were conducted for meropenem, colistin and three combinations (Colistin:Meropenem_1:3, Colistin:Meropenem_1:1 and Colistin:Meropenem_3:1) against *A. baumannii* N16870 and *P. aeruginosa* 19147. All experiments were performed with an initial inoculum of ~$10^6$ CFU/mL in 20 mL of Cation-Adjusted Mueller-Hinton Broth (CAMHB) in 50 mL pyrogen-free and sterile polypropylene tubes. Serial samples (50 µL) were collected at 0, 1, 2, 4, and 24 h for viable counting on nutrient agar plates and the limit of detection was 20 CFU/mL. A ProtoCOL automated colony counter (Synbiosis, Cambridge, United Kingdom) was used to quantify bacteria after 24 h of incubation at 37° C. Bacterial growth was measured after 0, 1, 2, 4 and 24 h of incubation at 37° C. A growth control without antibiotic was also tested.

Spray Drying

A Büchi 290 spray dryer (Büchi Labortechnik AG, Falwil, Switzerland) was employed to produce the composite particles at the following parameters: inlet temperature 110° C.; outlet temperature 63° C.; aspirator 35 m$^3$/h; atomizer setting 700 L/h; feed rate 2 mL/min. The total solid content of the feed solutions was 13.3 mg/mL for all formulations. The feed solutions for the composite formulations were prepared by dissolving colistin and meropenem at the mass ratios of 3:1, 1:1 and 1:3 in water. The spray-dried samples were stored in a desiccator with silica gel at 20±3° C.

Scanning Electron Microscopy (SEM)

Samples were visualized using a scanning electron microscope (NOVA nanoSEM, FEI Company, Hillsboro, Oreg., USA). Adhesive carbon tape was put on the stainless steel stub and then the formulations were scattered over the tape. A thin film of platinum was coated on the stubs using a sputter coater (208 HR, Cressington Sputter Coater, England, UK). The images were captured using built-in software.

Particle Size Distribution

Image analysis based on SEM micrographs was used for particle sizing. Martin's diameter was measured as the indicator of physical particle size (n=100) and $D_{10}$, $D_{50}$ and $D_{90}$ were calculated.

Powder X-Ray Diffraction (P-XRD)

Powder X-ray diffraction (Rigaku Americas, Tex., USA) was applied to evaluate crystallinity of the powders. Each powder formulation was spread on a glass slide and the XRD patterns were obtained from 5 to 40° 2θ.

Specific Surface Area and Pore Volume

Surface area and pore volume were measured using a TriStar3000 BET equipment (Micromeritics Instrument Company, Norcross, Ga.). Approximately 300 mg of each sample was filled into a BET sample tube and degassed overnight. Nitrogen with high purity was used as the adsorbate, and the adsorption behavior at varying relative pressure conditions was measured. The specific surface areas and pore volume of three replicates were determined.

Time-of-Flight Secondary Ion Mass Spectrometry (ToF-SIMS)

Surface composition of the composite formulations was characterized using Time-of-flight secondary ion mass spectrometry (nanoToF instrument, Physical Electronics Inc., Chanhassen, Minn., USA) as described elsewhere with slight modifications (Zhou Q. et al., *J. Pharm. Sci.* 2011, 100, 3421-3430). Data were obtained from 4 areas (100×100 m each) per sample. Characteristic peak fragments for azithromycin and L-leucine were identified. For colistin, the peaks at m/z ~30 atomic mass unit (amu) and ~86 amu, corresponding to $[CH_4N^+]$ and $[C_5H_{12}N^+]$ fragments, respectively, were selected. For meropenem, the fragment at m/z~68 amu corresponding to $[C_4H_6N^+]$ was selected as the characteristic peak. Sample spectra were processed using the WincadenceN software (Physical Electronics Inc., Chanhassen, Minn., USA) to construct high-resolution surface composition maps.

X-Ray Photoelectron Spectroscopy (XPS)

The surface composition of the composite formulations was evaluated quantitatively using X-ray photoelectron spectroscopy (XPS) (AXIS Ultra DLD spectrometer, Kratos Analytical Inc., Manchester, UK). The detailed XPS method was described previously. A CasaXPS software (version 2313 Dev64) was applied to process the XPS data. Curve-fitting was performed following a Shirley background subtraction using model peaks obtained from pure compounds. The atomic concentrations of the elements in the near-surface region were estimated after a Shirley background subtraction taking into account the corresponding Scofield atomic sensitivity factors and inelastic mean free path (IMFP) of photoelectrons using standard procedures in the CasaXPS software assuming homogeneous mixture of the elements within the information depth (~10 nm).

Fourier Transform Infrared Spectroscopy (FTIR)

The spray-dried powders were analyzed using an FTIR with attenuated total reflectance (ATR) (Cary 600 series FTIR spectrometer, Agilent Technologies, Santa Clara, Calif., USA). A small amount of powder was carefully placed onto the ATR crystal, and the pressure disk was used to improve the uniformity of contact between the sample and the ATR crystal of the instrument. Samples were analysed at a resolution of 4 cm$^{-1}$. A background scan was collected initially, and the sample spectrum was collected subsequently with the built-in software automatically subtracting the background.

In-Vitro Aerosol Performance

A Multi-Stage Liquid Impinger (MSLI) (Copley Scientific Limited, Nottingham, UK) was used to evaluate in-vitro aerosol performance with a USP induction port (USP throat). Each sample (10±2 mg) was loaded into a capsule (size 3 hydroxypropyl methylcellulose capsules, Qualicaps, Whitsett, N.C., USA) and aerosolized by an RSO1 DPI device (Plastiape S.p.A., Osnago, Italy). Aerosol performance of the formulations was tested using a standard dispersion procedure: 4 L of air was drawn to pass the inhaler at an airflow of 100 L/min for 2.4 s, with a pressure drop of ~4 kPa across the device. Under these experimental conditions, the cutoff diameters for Stages 1, 2, 3 and 4 of MSLI were 10.4, 4.9, 2.4, and 1.2 m, respectively. Drug retained in capsule, device, USP throat, Stages 1-4 and filter paper were dissolved using a 20 mL of water and quantified. Emitted dose (ED) was defined as the collected drug except for those retained in the capsule and device, over the total recovered drug. Fine particle fraction (FPF) represents the fraction of the drugs deposited on Stage 3, Stage 4 and filter paper over the recovered dose.

Drug Quantification

Concentrations of colistin sulfate and meropenem were determined using a validated HPLC method. Briefly, the HPLC system consisted of pump (1260 Quat Pump VL), thermostate (1290 Thermostate), autosampler (1260 ALS), thermostated column compartment (1260 TCC), variable wavelength detector (1260 VWD) (Agilant, Waldbronn, Germany), and a 5 µm, C18 separation column (150×4.60 mm, Agilant, Waldbronn, Germany). The mobile phase consisted of 30 mM sodium sulfate (adjusted to pH 2.5 with $H_3PO_4$) (A) and acetonitrile (B). The isocratic elution program used for colistin and meropenem detection was 76% A and 24% v/v for 7 min at the flow rate of 1.0 mL/min. The absorbance profile of both colistin and meropenem was monitored at 214 nm. Calibration curves prepared for colistin (0.0125-0.5 mg/mL) and meropenem (0.0125-0.5 mg/mL) in water were linear ($r^2>0.999$).

Statistical Analysis

One-way analysis of variance (ANOVA) with the Tukey-Kramer post-hoc test was employed for statistical analysis using a GraphPad Prism software (GraphPad Software, Inc., La Jolla, Calif., USA). The asterisks denote the statistical differences of groups as indicated on figures as *$p<0.05$, $p<0.01$, *$p<0.001$, ****$p<0.0001$ and NS for not significant ($p>0.05$).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A dry powder composition consisting of colistin, or a pharmaceutically acceptable salt thereof, and meropenem, or a pharmaceutically acceptable salt thereof, wherein
   drug material colistin, or a pharmaceutically acceptable salt thereof, and meropenem, or a pharmaceutically acceptable salt thereof, are first dissolved in an aqueous or an organic medium to prepare a solution;
   and followed by
   spray-drying of said solution to afford said dry powder composition, wherein said colistin, or a pharmaceutically acceptable salt thereof, is enriched on the surface of the dry powder whereby said dry powder composition has a bactericidal efficacy with at least 4 log 10 reduction of Gram-negative bacteria in 24 hours.

2. The dry powder composition of claim 1, wherein said colistin, or a pharmaceutically acceptable salt thereof, and meropenem, or a pharmaceutically acceptable salt thereof, are in a ratio of about 1:10 to about 10:1 (weight/weight).

3. A method for treating a patient with a bacterial infection comprising the step of administering a therapeutically effective amount of the dry powder composition of claim 2, together with one or more optional carriers, diluents, or excipients, to a patient in need of relief from said infection.

4. The method according to claim 3, wherein said infection is an infection of the lungs.

5. The method according to claim 3, wherein said infection is caused by *Pseudomonas aeruginosa, Acinetobacter baumannii*, or *Klebsiella pneumoniae*.

6. The method according to claim 3, wherein said pharmaceutical composition is administered by inhalation.

7. A pharmaceutical composition consisting of the dry powder of claim 1 together with one or more pharmaceutically acceptable excipients.

8. The pharmaceutical composition of claim 7, wherein said colistin, or a pharmaceutically acceptable salt thereof, and meropenem, or a pharmaceutically acceptable salt thereof, are in a ratio of about 1:10 to about 10:1 (weight/weight).

9. A pharmaceutical composition consisting of colistin, or a pharmaceutically acceptable salt thereof, meropenem, or a pharmaceutically acceptable salt thereof, and one or more pharmaceutically acceptable excipients, wherein:
   colistin, or a pharmaceutically acceptable salt thereof, and meropenem, or a pharmaceutically acceptable salt thereof are first dissolved in an aqueous medium to prepare a solution together with one or more pharmaceutically acceptable excipients, which is followed by spray-drying said solution to afford a dry powder of said pharmaceutical composition, wherein said colistin, or a pharmaceutically acceptable salt thereof, is enriched on the surface of the dry powder, whereby the dry powder of said pharmaceutical composition has a bactericidal efficacy with at least 4 log 10 reduction of Gram-negative bacteria in 24 hours.

10. The pharmaceutical composition according to claim 9, wherein said solution of colistin, or a pharmaceutically acceptable salt thereof, and meropenem, or a pharmaceutically acceptable salt thereof, comprises about 5 to 200 mg of colistin, or a pharmaceutically acceptable salt thereof, and meropenem, or a pharmaceutically acceptable salt thereof, in a ratio of about 1:10 to about 10:1 (weight/weight) per milliliter.

11. The pharmaceutical composition according claim 9, wherein the dry powder of said pharmaceutical composition is for the treatment of a lung infection.

12. The pharmaceutical composition according claim 9, wherein the dry powder of said pharmaceutical composition is administered by inhalation.

13. A method for treating a patient with a bacterial infection comprising the step of administering a therapeutically effective amount of a pharmaceutical composition consisting of colistin, or a pharmaceutically acceptable salt thereof, meropenem, or a pharmaceutically acceptable salt thereof, and one or more pharmaceutically acceptable excipients, wherein:
   colistin, or a pharmaceutically acceptable salt thereof, and meropenem, or a pharmaceutically acceptable salt thereof are first dissolved in an aqueous medium to prepare a solution together with one or more pharmaceutically acceptable excipients, which is followed by spray-drying said solution to afford a dry powder of said pharmaceutical composition, wherein said colistin, or a pharmaceutically acceptable salt thereof, is enriched on the surface of the dry powder, whereby the dry powder of said pharmaceutical composition has a bactericidal efficacy with at least 4 log 10 reduction of Gram-negative bacteria in 24 hours.

14. The method according to claim 13, wherein said infection is an infection of the lungs.

15. The method according to claim 13, wherein said infection is caused by *Pseudomonas aeruginosa, Acinetobacter baumannii,* or *Klebsiella pneumoniae.*

16. The method according to claim 13, wherein said pharmaceutical composition is administered by inhalation.

* * * * *